United States Patent [19]

Mukhopadhyay et al.

[11] Patent Number: 5,001,258

[45] Date of Patent: Mar. 19, 1991

[54] ANTIBIOTIC, FUMIFUNGIN, A MICROBIAL PROCESS FOR THE PREPARATION THEREOF, AND THE USE THEREOF AS A PHARMACEUTICAL

[75] Inventors: Triptikumar Mukhopadhyay; Kirity Roy, both of Bombay, India; Hans-Wolfram Fehlhaber, Idstein/Taunus; Richard H. Rupp, Königstein/Taunus, both of Fed. Rep. of Germany; Bimal N. Ganguli, Bombay, India

[73] Assignee: Hoechst Aktiengesellschaft, Frankfurt, Fed. Rep. of Germany

[21] Appl. No.: 210,373

[22] Filed: Jun. 23, 1988

[30] Foreign Application Priority Data

Jun. 25, 1987 [DE] Fed. Rep. of Germany ....... 3720981

[51] Int. Cl.$^5$ .............................................. C07C 67/02
[52] U.S. Cl. .................... 560/252; 435/106; 514/546
[58] Field of Search .................. 560/252; 435/106; 514/546

[56] References Cited

U.S. PATENT DOCUMENTS 3,394,171 7/1968 Thompson ........................... 560/252
4,273,721 7/1981 Nersesion ........................... 560/252

FOREIGN PATENT DOCUMENTS 255126 2/1988 European Pat. Off. .
1022337 1/1989 Japan .

OTHER PUBLICATIONS

Aragozzini, F., et al., Isolation and Structure Determination of a New Antifungal etc., Tetrahedron, vol. 28, pp. 5493-5498, 1972.

Aragozzini, F., et al., Biosynthesis of the Antibiotic Thermozymocidin J. C. S. Chem. Comm., pp. 788-789, 1973.

Kuo, D. H. and Wendler, N. L., Total Synthesis of the Chiral Lactone Derived etc., Tetrahedon Letters No. 3, pp. 211-214, 1978.

*Primary Examiner*—Paul J. Killos
*Attorney, Agent, or Firm*—Finnegan, Henderson, Farabow, Garrett and Dunner

[57] ABSTRACT

Fumifungin, a compound of the formula

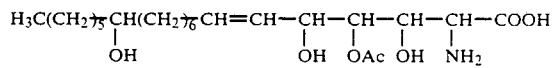

can be isolated from the culture broth of fungus culture No. Y-83,0405 (DSM 4152), and has bactericidal and fungicidal properties.

3 Claims, No Drawings

ANTIBIOTIC, FUMIFUNGIN, A MICROBIAL PROCESS FOR THE PREPARATION THEREOF, AND THE USE THEREOF AS A PHARMACEUTICAL

DESCRIPTION

A new antibiotic, fumifungin, a microbial process for the preparation thereof, and the use thereof as a pharmaceutical The present invention relates to a new antibiotic, called fumifungin, and to a process for the preparation thereof from the fungus culture No. Y-83,0405 and the mutants and variants thereof.

Fumifungin can be called 2-amino-4-acetoxy-3,5,14-tri-hydroxy-$\Delta^6$-eicosenoic acid and has the following structural formula:

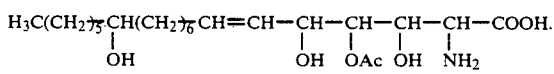

Other antibiotics from this group, which are reported in the literature and which, however, differ from fumifungin, are thermozymocidin and/or myriocin.

Thermozymocidin is described in Tetrahedron 28, 5493, 1972, Chemical Communications 788, 1973, Tetrahedron Letters 211, 1978 and in Belgian Patent No. 796,682. Myriocin is described in the Journal of Antibiotics, 25, 109, 1972, Journal of Organic Chemistry, 38, 1253, 1973 and in U.S. Pat. No. 3,928,572.

Descriptions of thermozymocidin and myriocin are also to be found in the CRC Handbook of Antibiotic Compounds, Vol. VI, pages 391-418, in the section "Fatty Acid Derivatives" as well as in "Fungal Metabolites II" by W. B. Turner & D. C. Aldridge, Academic Press 1983, pages 173-175. The organism producing thermozymocidin has been described as the thermophilic Ascomycetes Myriococcum albomyces. However, all the available characteristic data indicate that fumifungin differs distinctly from thermozymocidin and myriocin and all other known antibiotics.

The fungus culture No. Y-83,0405 used for the production of fumifungin was isolated from a soil sample taken in the Himalayas in India and has been identified by its physiological, biochemical and morphological properties, by known methods, as Aspergillus fumigatus Fresenius 1863.

It was deposited on June 23, 1987, at the "Deutsche Sammlung von Mikroorganismen" (German Microorganism Collection) (Göttingen) under entry number DSM 4152.

The present invention also relates to a process for the preparation of the new antibiotic fumifungin. This process comprises the cultivation of fungus culture No. Y-83,0405, or the mutants and variants thereof, under aerobic conditions on a nutrient medium which contains sources of carbon and nitrogen, inorganic nutrient salts and trace elements, and the isolation and purification of this antibiotic from the culture broth.

Suitable sources of carbon are glucose, sucrose, starch or dextrin. Glucose is the preferred source of carbon. Suitable sources of nitrogen are soybean meal, tryptone, yeast extract, beef extract, malt extract, corn-steep liquor, peptone or inorganic substances such as ammonium salts. Malt extract or a combination of malt extract with other sources of nitrogen is preferred as such. Possible inorganic nutrient salts are sodium chloride, potassium hydrogen/dihydrogen phosphate or calcium carbonate. The trace elements which can be present are salts of iron, manganese, copper, zinc, cobalt or other such heavy metals.

The culture No. Y-83,0405 can be cultivated at temperatures between 24° C. and 30° C. and at a pH between 6.0 and 8.0. The culture No. Y-83,0405 is preferably cultivated at 26° C. ($\pm 1°$ C.) and pH 6.5.

The cultivation is carried out for 66 to 96 hours, after which time an optimal yield of the antibiotic according to the invention is obtained. The fermentation is preferably carried out for 90 hours under submerged conditions in shaken flasks. The progress of the fermentation and the formation of the fumifungin according to the invention can be followed by measurement of the bioactivity of the culture broth against Bacillus subtilis, Candida albicans and Aspergillus niger by the known agar plate diffusion determination method.

Fumifungin is present in the resulting culture broth both in the culture filtrate and in the mycelium cake. Fumifungin is preferably isolated from the culture filtrate, which is separated from the mycelium by centrifugation. It can be obtained from the culture filtrate by one or more known methods, such as extraction using solvents which are immiscible with water, such as n-BuOH, or adsorption on adsorbents such as active charcoal, Diaion HP-20 ® or Amberlite XAD-2 ®. The preferred method is adsorption on Diaion HP-20 ® and subsequent desorption of the compound using suitable organic solvents. Organic solvents suitable for this purpose are methanol, acetone or acetonitrile, as well as aqueous combinations of these solvents. Stepwise elution with (1) MeOH:H$_2$O (1:1) and then MeOH:H$_2$O (8:2) as solvents is preferred for the process according to the invention. The fumifungin obtained from Diaion HP-20 ® by elution with MeOH:H$_2$O (8:2) can be further processed by, for example, evaporation of the total volume to dryness, or extraction of the eluates with n-BuOH, or readsorption of the diluted eluates on resins such as Diaion HP-20 ® or Amberlite XAD-2 ®. The preferred method comprises concentrating the eluates in vacuo in order to remove much of the organic solvent, diluting the resulting concentrate with demineralized water, and readsorbing the resultant solution on Diaion HP-20 ®, followed by desorption with MeOH:H$_2$O (6:4) and then 100% pure MeOH. Removal of the solvent from the active eluates provides crude fumifungin. Final purification can be achieved by chromatography on substrates such as silica gel, modified silica gels, cellulose or LH-20, or by crystallization of the crude fumifungin from organic solvents or aqueous mixtures thereof, or by a combination of these methods. In the preferred method, the crude fumifungin is chromatographed on a column packed with modified silica gel (dimethyloctadecylsilylated silica gel 50 $\mu$), which is called RP-18 hereinafter, and eluted under pressure by the method known as medium pressure liquid chromatography (MPLC).

Among the various solvents for elution from RP-18, such as methanol, acetonitrile or acetone or aqueous mixtures thereof, it is preferable to use for the stepwise elution initially MeOH:H$_2$O (6:4) and then MeOH:H$_2$O (7:3). The removal of the solvent from the active eluates in vacuo, and complete freeze-drying provides fumifungin as a colorless solid.

The examples which follow serve to illustrate the present invention:

Example I

Isolation of the Culture Y-83,0405 from Soil

Composition of the nutrient medium for isolation

| | |
|---|---|
| Glucose | 40 g |
| Peptone | 10 g |
| Agar | 15 g |
| Demineralized water | 1 liter |
| Chloramphenicol | 0.05 g |
| Cycloheximide | 0.2 g |
| pH | 9.0 |

When preparing the above medium, chloramphenicol and cycloheximide are added last. A solution of the chloramphenicol in 10 ml of 95% pure ethanol is added to the medium and thoroughly mixed in. Then a solution of cycloheximide in 10 ml of acetone is added to, and thoroughly mixed with, the medium. The latter is autoclaved at a temperature of 121° C. for 10 minutes. The pH was 9.0 before autoclaving and 7.0 thereafter.

50 ml portions of the sterilized medium which has been cooled to 45° C. are poured into 150 mm Petri dishes and left to solidify.

The fungus culture No. Y-83,0405 was isolated in a known manner from the soil sample from the Himalayas by the soil-dilution method and streaking of the above medium.

Example II

Maintenance of the Strain of the Culture Y-83,0405

The culture No. Y-83,0405 is maintained on Sabouraud's glucose-agar medium of the following composition:

| | |
|---|---|
| Glucose | 40 g |
| Peptone | 10 g |
| Na$_2$HPO$_4$ | 1 g |
| Agar | 15 g |
| Demineralized water | 1 liter |
| pH | 6.5 |

After the ingredients have been completely dissolved by heating, the medium is distributed over test tubes and then sterilized at 121° C. for 20 minutes. The test tubes are left to cool for solidification of the medium. Agar slants are inoculated with spores of the culture No. Y-83,0405 and incubated at 26° C. (±1° C.) until satisfactory sporulation is observed. The cultures with satisfactory sporulation are stored in a refrigerator.

Example III

Fermentation of the Culture Y-83,04505 in Shaken Flasks

Composition of the seed culture medium

| | |
|---|---|
| Soluble starch | 15 g |
| Soybean meal | 15 g |
| Glucose | 5 g |
| CaCO$_3$ | 2 g |
| NaCl | 5 g |
| Yeast extract | 2 g |
| Cornsteep liquor | 1 g |
| Demineralized water | 1 liter |
| pH | 6.5 |

100 ml portions of the above seed culture medium are distributed over wide-necked 500 ml Erlenmeyer flasks and sterilized at 121° C. for 20 minutes. The flasks are cooled and then inoculated with a few platinum loops full of the abovementioned culture with satisfactory sporulation and are shaken at 26° C. (±1° C.) and 240 rpm for 60 hours, during which satisfactory growth is observed. The seed culture obtained in this way is used for inoculation of the production medium of the following composition.

Composition of the production medium:

| | |
|---|---|
| Glucose | 10 g |
| Malt extract | 20 g |
| Peptone | 10 g |
| Na$_2$HPO$_4$ | 1 g |
| ZnSO$_4$.7H$_2$O | 0.22 mg |
| CaCl$_2$ | 0.55 mg |
| MnCl$_2$.4H$_2$O | 0.5 mg |
| FeSO$_4$.5H$_2$O | 0.16 mg |
| CoCl$_2$.6H$_2$O | 0.16 mg |
| Demineralized water | 1 liter |
| pH before sterilization | 6.5 |
| pH after sterilization | 6.3 |

200 ml portions of the above production medium are distributed over 1 liter Erlenmeyer flasks and sterilized at 121° C. for 20 minutes. The flasks are cooled and then inoculated with the above seed culture medium (1% V/V). The fermentation is carried out at a temperature of 26° C. (±1° C.) in a rotary shaker at 220rpm for 90 hours.

The production of fumifungin is checked by the profile of activity against *Bacillus subtilis, Candida albicans* and *Aspergillus niger*. After harvesting, the culture broth is centrifuged, and the fumifungin is isolated from the culture filtrate and purified as described in Example IV.

Example IV:

Isolation and Purification of Fumifungin

About 60 liters of the fermentation broth are centrifuged to separate the mycelium from the culture filtrate.

The culture filtrate (55 liters) is adjusted to pH 5.9 and passed through a column packed with Diaion HP-20® (1.8 liters). The column is washed with demineralized water (7 liters). Elution with 50% strength methanol in water (20 liters) removes dark-colored inactive impurities.

The Diaion HP-20 ® column is then eluted with 80% strength methanol in water. The first fractions (2×800 ml) are inactive but the subsequent fractions (12×800 ml) show activity. The active eluates are concentrated under reduced pressure to a concentrate of 7 liters. Continuation of elution with 80% strength methanol in water (10×800 ml) yields no further activity. The concentrate is diluted by addition of 15 liters of demineralized water. The diluted solution is again passed through Diaion HP-20 ® (1 liter) and washed with 60% strength methanol in water (10 liters). The methanol/water is sucked completely out of the column, which is then eluted with methanol (4 liters). Removal of the solvent under reduced pressure and subsequent freeze-drying yields 1.5 g of crude fumifungin.

The crude fumifungin (600 mg) is subjected to medium pressure liquid chromatography using RP-18 as reverse phase support material. The column is eluted with 60% strength methanol in water at a flow rate of 11 ml/min until one liter of eluate has run out. The eluent is then changed to 70% methanol in water. The active fractions are combined, concentrated under reduced pressure and freeze-dried, resulting in 100 mg of pure colorless fumifungin.

The physicochemical properties of fumifungin are listed in Table I.

TABLE I

| Physicochemical properties of fumifungin | | | | |
|---|---|---|---|---|
| 1. Appearance | colorless powder | | | |
| 2. Solubility | methanol, DMSO | | | |
| 3. Elemental analysis | calc. C, | 61.25%, | found C, | 58.9% |
| | H, | 9.51% | H, | 9.5% |
| | N, | 3.20% | N, | 3.2% |
| 4. Molecular formula | $C_{22}H_{41}NO_7$ | | | |
| 5. Molecular weight | 431 | | | |
| 6. Melting point | 108° C. | | | |
| 7. Color reaction | (a) $KMnO_4$ - decoloration | | | |
| | (b) ninhydrin - violet color | | | |
| 8. UV (MeOH) | end absorption | | | |
| 9. IR (Nujol) | 3300, 3000, 1725, 1640, 1570, 1400, 1350, 1240, 1090, 975, 770, 730 $cm^{-1}$. | | | |
| 10. $^1$H NMR (CD$_3$OD) | 0.9, t (J = 6 Hz), 3H | | | |
| | 1.2-1.5, m broad, 20H | | | |
| | 2.05, s, 3H, | | | |
| | 2.1, m, 2H, | | | |
| | 3.5, s broad, 1H | | | |
| | 3.76, d(J = 4 Hz), 1H | | | |
| | 3.82, d(J = 6 Hz), 1H | | | |
| | 4.16, dd (J = 2 & 4 Hz), 1H | | | |
| | 5.33-5.4, m, 2H | | | |
| | 5.83-5.95, m, 1H | | | |

The new compound fumifungin has bactericidal and fungicidal properties. The minimum inhibitory concentrations (MIC) of fumifungin required to inhibit the growth of various strains of fungi are listed in Table II which follows:

TABLE II

| | MIC values for fumifungin | |
|---|---|---|
| Ser. No. | Test strains | MIC values in g/l |
| 1. | Candida albicans | 62.5 |
| 2. | Saccharomyces cerevisiae | 62.5 |
| 3. | Wild yeast | 62.5 |
| 4. | Aspergillus niger | >7.8 |
| 5. | Penicillium digitatum | >7.8 |
| 6. | Trichophyton mentagrophytes | >15.6 |
| 7. | Botrytis cinerea | 250 |
| 8. | Fusarium culmorum | 250 |
| 9. | Alternaria solani | 31.2 |
| 10. | Cercospora beticola | 0.9 |
| 11. | Cladosporium resinae | >0.9 |
| 12. | Piricularia oryzae | 125 |

We claim:

1. A compound of the formula

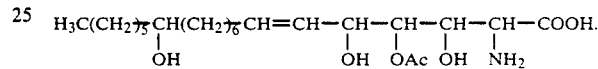

2. A pharmaceutical which contains a compound as claimed in claim 1, together with pharmaceutically acceptable carriers.

3. A method of preparing pharmaceuticals having antibiotic action comprising incorporating into said pharmaceuticals the compound claimed in claim 1.

* * * * *